(12) United States Patent
Ramaswamy et al.

(10) Patent No.: US 6,247,370 B1
(45) Date of Patent: Jun. 19, 2001

(54) TWO DIMENSIONAL STRESS RELAXATION TESTING DEVICE

(75) Inventors: Sanjeevi Ramaswamy; Naresh Mandyam Deivasigamani; Arumugam Viswanathan; Somanathan Narayana Sasthri; Muthukrishnan Subramaniam; Kalaiarasu Krishnaswamy, all of Chennai (IN)

(73) Assignee: Council of Scientific and Industrial Research, New Delhi, IN (US)

( * ) Notice: Subject to any disclaimer, the term of this patent is extended or adjusted under 35 U.S.C. 154(b) by 0 days.

(21) Appl. No.: 09/362,282

(22) Filed: Jul. 27, 1999

(30) Foreign Application Priority Data

Jan. 25, 1999 (IN) ............................... 137/DEL/99

(51) Int. Cl.[7] ................................ G01N 3/02; G01N 3/00
(52) U.S. Cl. ................................................ 73/857; 73/798
(58) Field of Search ........................... 73/818, 819, 798, 73/856, 857, 860

(56) References Cited

U.S. PATENT DOCUMENTS

| 4,497,206 | * | 2/1985 | Scheurenbrand | 73/382 R |
| 4,631,995 | * | 12/1986 | Vroenen | 82/164 |
| 4,665,625 | * | 5/1987 | Ireland et al. | 33/530 |
| 4,819,486 | * | 4/1989 | Kunkel et al. | 73/382 R |
| 5,448,918 | * | 9/1995 | Tucchio | 73/819 |
| 5,465,605 | * | 11/1995 | Smith et al. | 73/7 |

FOREIGN PATENT DOCUMENTS

| 3617455 | 11/1987 | (DE) . |
| 1125807 | 9/1968 | (GB) . |

* cited by examiner

Primary Examiner—Max Noori
(74) Attorney, Agent, or Firm—Ladas & Parry

(57) ABSTRACT

The present invention relates to a two dimensional stress relaxation testing device in which a plus shaped sample is stretched in mutually perpendicular directions simultaneously to monitor the stress and also the relaxation process of any sheet material in both axes. In view of this advantage, the present device provides the closest approximation to the in situ failure of the material.

15 Claims, 2 Drawing Sheets

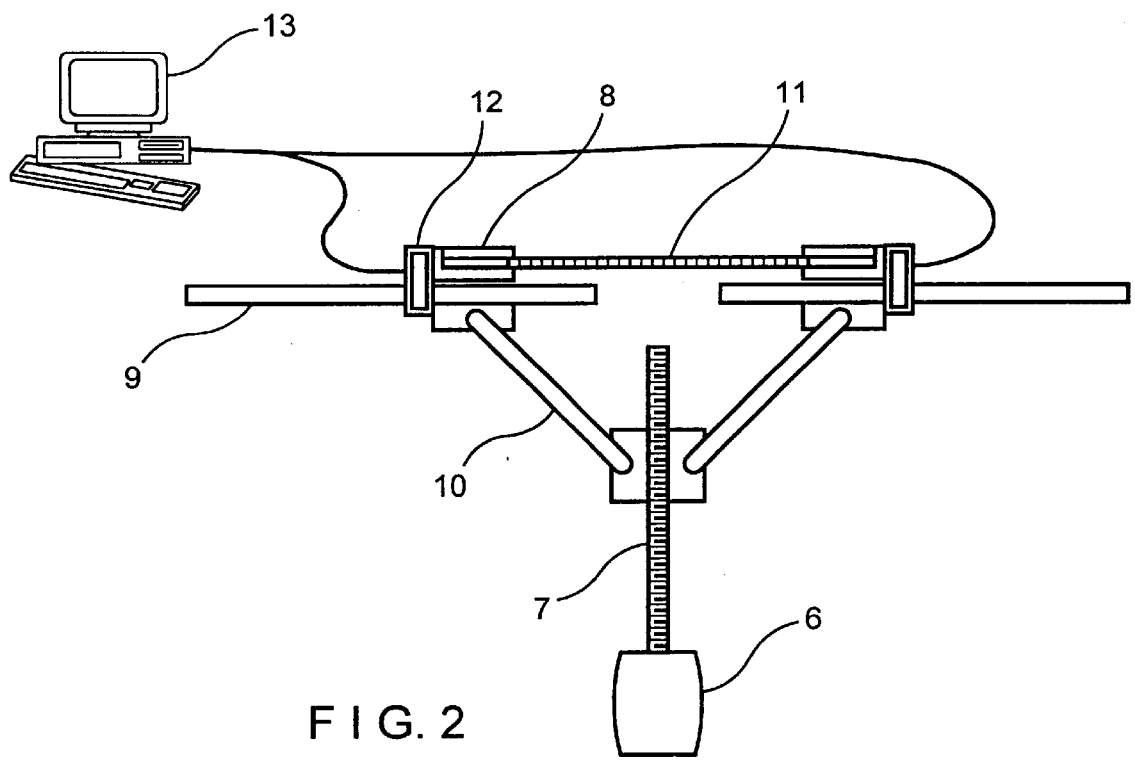
F I G. 2
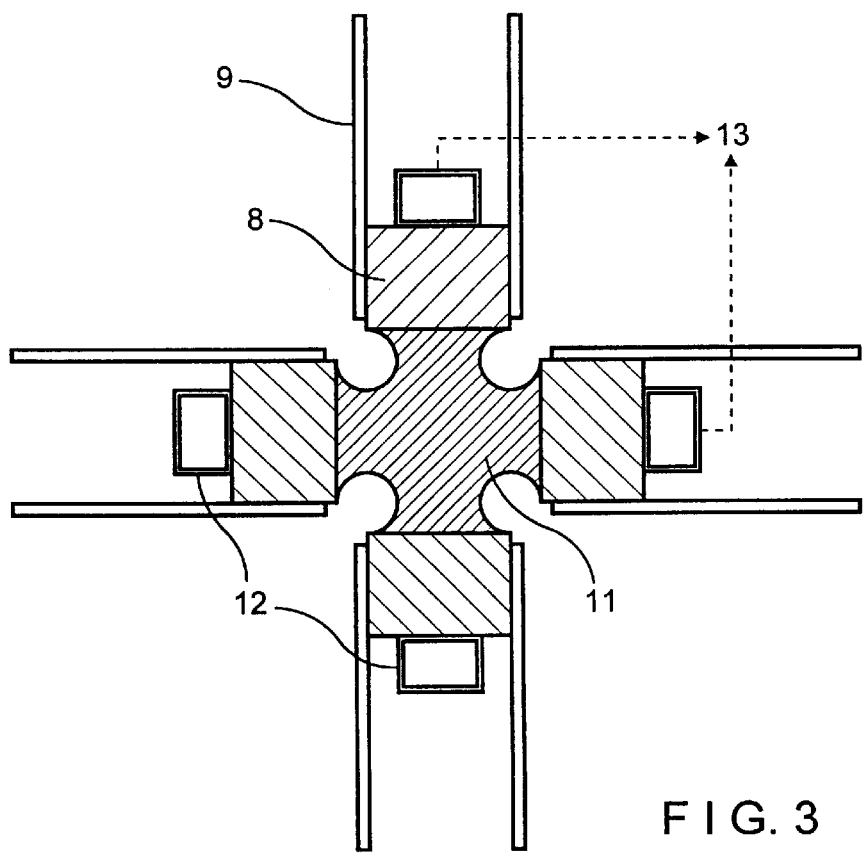
F I G. 3

TWO DIMENSIONAL STRESS RELAXATION TESTING DEVICE

FIELD OF THE INVENTION

The present invention relates to a two-dimensional stress relaxation testing device. The two-dimensional stress relaxation testing device has a potential industrial application as a quality control equipment in respect of such prominent industries like leather products, footwear, textile, polymeric industry to name but a few. Sheet materials like leather, polymers and textiles, under different application environments such as mechanical, thermal and hygrometric conditions exhibit various degrees of resiliance, shape retention, plastic set etc. This behavior of the above materials can be studied by analyzing their two dimensional stress relaxation which in turn would help in predicting its failure mechanism under actual application conditions.

BACKGROUND OF THE INVENTION

Several sheet materials like polymeric materials, leathers, textiles, engineering composite materials etc. are being widely used in several engineering environments. As reported by Ramanathan et al (Journal of the Indian Leather Technologists Association, 16, 293, 1968), these materials undergo various stresses in mutually perpendicular directions while in use for different applications. For example, the upper leather of a shoe is subjected to force in all directions. Ramanathan et al (Proceedings of the International Southern Biomedical Engineers Conference, Shrevepor, La., USA, p. 1, 1982) reported that the force on the surface of the upper portion of leather is enormous while walking. Moreover, with the advent of fashions several combination of materials are being used in shoe manufacture. It is therefore necessary to understand the mechanical properties, stress relaxation, hysteresis and mechanism of failure of these materials by simulating the user conditions for efficient use of these materials.

Presently the viscoelastic nature of materials is analysed by unidirectional testing using Universal Testing Machines (UTM), where a dumbbell shaped sample (1) gripped by two jaws (2) is pulled apart using motorized crosshead (3) till the sample fails, while the force developed during the process is sensed by a force transducer (5) and recorded by a recording device (4). As reported by Ridge and Wright (Biorheology, 2,67,1964), Muthiah et al (Biorheology, 4,185,1967), the force generated per unit area during the deformation, which eventually leads to the fracture of the sample, is usually taken as a measure of the tensile strength of the material under consideration. In addition, the gradual decrease in the force, developed during deformation, to a given strain level, viz., stress relaxation, provides information on the rearrangements of the molecular structure within the sample, which depends on their viscous nature, as reported by Arumugam et al (Handbook of Advanced Materials Testing, Edited by N P Cheremisinoff and P N Cheremisinoff, Marcel Dekker Inc., New York, p 909, 1995). Similarly repeated deformations up to a certain strain level and back provide information about the plasticity of the sample, as reported by Vogel (Bioengineering and Skin, 4, 75,1988). Vogel (Journal of Medicine, 7, 177, 1976) has developed a theoretical model for the stress relaxation process for rat skin using uniaxial samples. As reported by Arumugam (Ph. D. Thesis, University of Madras, 1989) and Arumugam et al (Journal of Biosciences, 19, 307,1994), all these characteristics depend on the rate at which the experiments are performed. Ambrazyavi et al (Pat. No. SU 1226123 dt. 23/411986) have designed an apparatus to measure relaxation process after compression in polymers. Dzhunisbek et al (Pat. No. SU 998918 dt. 23/4/1983) have also fabricated a device to measure the compression based stress relaxation coupled with friction in polymers. Methods involving monitoring of fall in pressure to detect relaxation have also been attempted for polymers as disclosed in Pat. No. SU 354317. Modifications induced during the relaxation process such as mechanical reduction in the thickness of the sample have also been tried by Dubovik et al (Pat. No. SU 1186996 dt. 23/10/1985). The main limitation in all the above devices is that they are all designed to measure the relaxation process only along a single axis or dimension.

In actual user conditions materials are generally exposed to forces acting in more than one dimension, which includes bending and stretching. Hence, the use of unidirectional sample for predicting the conditions for failure does not simulate the actual user conditions. In other words, deduction of realistic information and predicting or computing the mechanism of the failure of these viscoelastic materials from unidirectional tests has its limitations because of their high Poisson's ratio. For example, there is tremendous amount of lateral contraction due to the high Poisson's ratio of the leather while testing the sample in the conventional UTMs. Therefore, the extension and the breaking load observed for the sample under unidirectional test conditions are very different from the shoe undergoing a similar kind of stress during usage. Moreover, intermediate conditions of testing and the formation of surface cracks and their role in hastening or delaying failure during application cannot be studied by hitherto known techniques. In addition, there are inherent inhomogeneities in certain materials like leather, textiles etc., which necessitate performing uniaxial testing in more than one direction to get a complete understanding of the material properties.

The main object of the present invention is to provide a two dimensional stress relaxation testing device, which obviates the drawbacks stated above.

Another object of the present invention is to analyze stress related behavior like relaxation, hysteresis, fatigue and creep of materials simultaneously in two mutually perpendicular directions.

Yet another object of the present invention is to perform dynamic testing of materials Still another object of the present invention is to reduce the number of test samples and time as well as labor while analyzing the stress related properties of materials.

Yet another object of the present invention is to study the mechanical properties of sheet materials without any lateral contraction.

Still another object of the present invention is to develop a device to provide accurate information on the failure of the materials as the lateral contraction is not present.

SUMMARY OF THE INVENTION

The main principle involved in this invention lies in using two pairs of juxtaposed grippers, mutually perpendicular to each other for holding the test specimen, thereby enabling the simultaneous measurement of stress related properties, especially stress relaxation of materials, avoiding the factor of Poisson's ratio, in mutually perpendicular directions while simulating the near exact application conditions of different materials of multifarious characteristics.

BRIEF DESCRIPTION OF THE ACCOMPANYING DRAWINGS

In the drawings accompanying this specification,

FIG. 2 is an elevational view of the device of the present invention; and

FIG. 3 is a the plan view of the device of the present invention

Figures 1A, 1B:
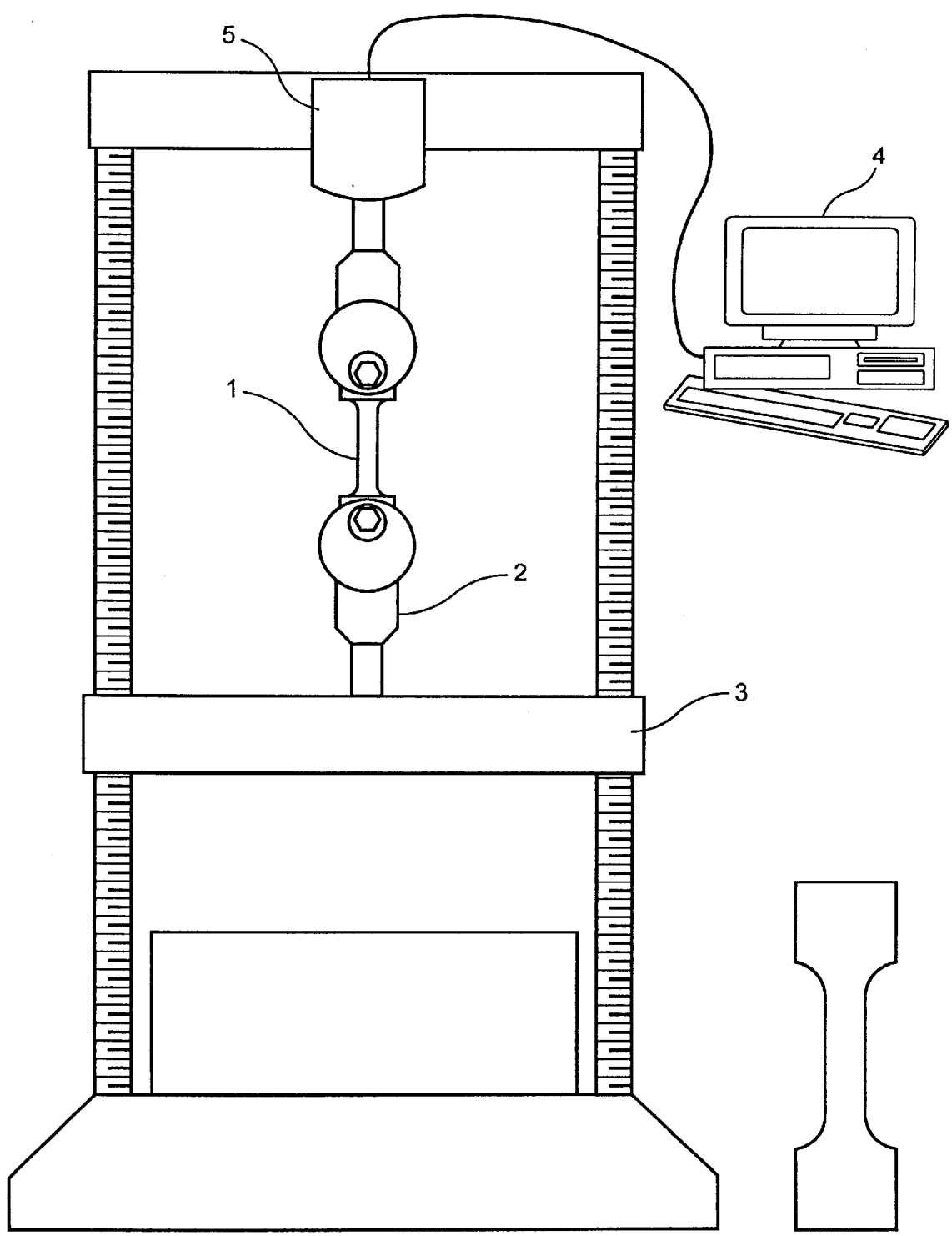
FIG. 1A shows a conventional tensile testing machine (UTM)
FIG. 1B shows a typical uniaxial sample of the prior art.

Various components, as shown with numerals in the FIG. 1A of the drawings accompanying this specification, are the following:

1 refers to the dumbbell shaped sample
2 refers to the jaws
3 refers to the cross-head
4 refers to the recording device and
5 refers to the force transducer Various components, as shown with numerals in the FIG. 2 as well as FIG. 3 of the drawings accompanying this specification, are the following.

6 refers to the driving source.
7 refers to the shaft connected to the driving source.
8 refers to the grippers.
9 refers to the slide ways, on which the grippers slide away from each other.
10 refers to the arms connecting the shaft and the grips.
11 refers to the specimen to be tested.
12 refers to the force detector and
13 refers to the attached output device.

The device of the present invention comprises essentially a forearm mechanism which is driven by a driving source to move two pairs of grippers away from each other on slideways.

Accordingly, the present invention provides a two dimensional stress relaxation testing device which comprises two pairs of juxtaposed grippers (8), mutually perpendicular to each other for holding the test specimen (11), each gripper being provided with a thimble to eliminate any slackness while testing, the grippers being driven over four slideways (9), away from each other, through forearm linkage mechanism, each arm (10) displacing one gripper slide in a horizontal plane, with the drive being fed by a shaft (7) from a driving source (6) and the force generated thereby being detected by four force detectors (12) mounted on a clamp, displaying the output in an output device (13), connected to an interface.

DESCRIPTION OF THE PREFERRED EMBODIMENTS

In an embodiment of the present invention, the test specimen used may be selected from any sheet material from the group consisting of leather, polymer, textile, rubber and any composite thereof.

In another embodiment of the present invention, the driving source may be selected from the group consisting of D.C. (Direct Current) motor, hydraulic drive and pneumatic drive.

In yet another embodiment of the present invention, the speed of separation of the grips may be in the range of 0.01 mm to 1000 mm per second.

In still another embodiment of the present invention, the gauge length used along two mutually perpendicular axes may be at least 5 mm.

In yet another embodiment of the present invention, the grips used may be selected from the group consisting of mechanical, electrical, and pneumatic grips.

In still another embodiment of the present invention, the control mechanism for the movement of the grips may be selected from gear assembly, hydraulic drive, and pneumatic drive.

In yet another embodiment of the present invention, the force detectors may be selected from force transducers, and strain gauges In still another embodiment of the present invention, the output device used may be selected from the group consisting of computer interface, digital display, analog output, and chart recorder.

The device has two pairs of juxtaposed grippers (8), mutually perpendicular to each other for holding the test specimen. The grippers are designed to move away from each other on mutually perpendicular linear motion slideways (9). Each gripper slide is provided with a thimble to eliminate any slackness in the specimen before initiating the experiment. The test sample (11) is held by the grippers (8) and is stretched at a rate ranging from 0.01 mm to 1000 mm per second in equal amounts along two mutually perpendicular directions. The drive to the gripper slides is provided by a driving source (6) through a vertical shaft (7) and a forearm linkage (10) mechanism, each arm displacing one gripper slide in the horizontal plane. The force generated is detected and measured by the force detectors (12), which send the output to output device. The simultaneous measurement of the force in the two mutually perpendicular directions gives the two dimensional stress relaxation. The loss of energy owing to the repeated stress or strain cycling of the sample can also be computed from the hysteresis loop obtained on the output device.

The present invention will now be described with reference to the following illustrative but non-limitative examples:

EXAMPLE 1

A plus shaped test sample of length 20 mm in both the mutually perpendicular directions was cut with a die from a cow upper leather and the same was gripped to the device with the help of four mechanical grippers. The test sample was strained at 1 mm/min speed by using a DC motor as the driving source to 20% level and then the machine was switched off. The sample was allowed to relax for a period of 15 minutes, while continuously monitoring the force in the mutually perpendicular directions i.e., the X and Y axes, which was displayed. The values registered for both X and Y axes with time is given below in Table-1.

TABLE 1

| Time (sec.) | Load in X Axis(Kg) | Load in Y Axis (Kg) |
| --- | --- | --- |
| 0 | 6.15 | 10.2 |
| 15 | 2.5 | 7.8 |
| 30 | 1.7 | 7.3 |
| 45 | 1.6 | 7.1 |
| 60 | 1.3 | 7 |
| 120 | 1 | 6.8 |
| 180 | 0.8 | 6.7 |
| 300 | 0.5 | 6.5 |
| 900 | 0.45 | 6.4 |

EXAMPLE 2

A plus shaped test sample of length 50 mm in both the mutually perpendicular directions was cut with a die from a polyethylene film and the same was gripped to the device with the help of four mechanical grippers. The test sample was strained at 50 mm/min speed by using a DC motor as the driving source to 80% level and then the machine was switched off. The sample was allowed to relax for a period of 15 minutes, while continuously monitoring the force on the sample The results obtained for the mutually perpendicular directions viz., the X and Y axes are given in Table-2 below.

TABLE 2

| Time (sec.) | Load in X Axis(Kg) | Load in Y Axis(Kg) |
| --- | --- | --- |
| 0 | 4.74 | 3.53 |
| 15 | 3.4 | 2.5 |
| 30 | 3.1 | 2.3 |
| 45 | 3 | 2.2 |
| 60 | 2.9 | 2.2 |
| 120 | 2.8 | 2.1 |
| 180 | 2.7 | 2.1 |
| 300 | 2.7 | 2.1 |
| 900 | 2.7 | 2.1 |

EXAMPLE 3

A plus shapes test sample of length 70 mm in both the mutually perpendicular directions was cut with a die from a textile material and the same was gripped to the device with the help of four pneumatic grippers. The test sample was strained at 100 mm/min speed by using a DC motor drive to 20% level and then the machine was switch off. The sample was allowed to relax for a period of 1 hour, while continuously monitoring the force on the sample, which was displayed. The results obtained for the mutually perpendicular directions i.e., the X and Y-axes are given in table 3 below.

TABLE 3

| Time (sec.) | Load in X Axis (Kg) | Load in Y Axis (Kg) |
| --- | --- | --- |
| 0 | 12.41 | 13.84 |
| 15 | 7.6 | 8.7 |
| 30 | 7.3 | 8.5 |
| 45 | 7.2 | 8.2 |
| 60 | 7.1 | 8.1 |
| 120 | 7 | 8 |
| 300 | 6.9 | 7.9 |
| 1800 | 6.8 | 7.8 |
| 3600 | 6.8 | 7.8 |

The main advantages of the present invention are the following.

1. It is possible to study the stress relaxation behavior as well as hysteresis of different materials in two mutually perpendicular directions simultaneously, thereby reducing the number of test samples and testing time required thereof.

2. Stress relaxation experiments can be carried out without subjecting the test sample to lateral contractions seen in uniaxial tests. Thus the present method would give a more accurate and realistic data than the uniaxial tests by overcoming the limitation encountered in the materials with high Poisson's ratio. The sample data provided in Table 4 clearly brings out the dissimilarity between the two methods i.e., the faster rate of relaxation in the two dimensional test as against the uniaxial test for a goat upper leather.

TABLE 4

| | Load (Kg) | | |
| --- | --- | --- | --- |
| Time (sec) | Two-Dimensional (present method) | | Uniaxial (conventional) |
| | X-axis | Y-axis | |
| 0 | 6.15 | 10.2 | 1.22 |
| 15 | 2.5 | 7.8 | 1.10 |
| 30 | 1.7 | 7.3 | 1.08 |
| 60 | 1.3 | 7 | 1.05 |
| 120 | 1 | 6.8 | 1.04 |
| 300 | 0.5 | 6.5 | 0.99 |
| 900 | 0.45 | 6.4 | 0.96 |

3. It is also possible to study the role of fiber orientation in the stress relaxation and dynamic testing conditions wherein the samples are subjected to repeated stress or strain cycling at high speed.

4. It is also possible to study the fatigue and flexing properties of sheet materials, polymeric materials and leather.

5. The regional shape deformation in sheet materials, biological materials and leather can be studied in this instrument.

We claim:

1. A two dimensional stress relaxation testing device for testing a specimen, said device comprising:
   (a) first and second pairs of juxtaposed gripping means for holding the specimen, said first pair of juxtaposed gripping means being disposed perpendicular to the second pair of juxtaposed gripping means;
   (b) slideway means, comprising a slideway for each of the gripping means, for slidably guiding the first and second pairs of gripping means in mutually perpendicular directions in a horizontal plane;
   (c) drive means for displacing said first and second pairs of gripping means along the respective slideways in said mutually perpendicular directions, said drive means comprising a drive source, a shaft and linkage means for linking the drive source to each of the gripping means; and
   (d) detecting means for monitoring a force applied to said specimen in each of said mutually perpendicular directions.

2. A two dimensional stress relaxation testing device according to claim 1, wherein the drive means displaces said first and second pairs of gripping means in said mutually perpendicular directions at a constant rate.

3. A two dimensional stress relaxation testing device according to claim 2, wherein each of said gripping means comprises thimble means for eliminating slackness in the testing of the specimen.

4. A two dimensional stress relaxation testing device according to claim 3, wherein the detecting means comprises four force detectors with each of the force detectors being mounted on one of the gripping means.

5. A two dimensional stress relaxation testing device according to claim 4, wherein the detecting means comprises output display means for displaying an output of said detecting means.

6. An apparatus comprising the testing device of claim 1 and a test specimen comprising a material selected from the group consisting of leather, a polymer, a textile, and rubber.

7. A two dimensional stress relaxation testing device according to claim 2, wherein the constant rate is in the range of 0.01 mm to 1000 mm per second.

8. A two dimensional stress relaxation testing device according to claim 1, wherein a distance between the juxtaposed gripping means in the first and second pairs of juxtaposed gripping means is at least 5 mm.

9. A two dimensional stress relaxation testing device according to claim 1, wherein the gripping means comprise grippers selected from the group consisting of mechanical grippers, electric grippers and pneumatic grippers.

10. A two dimensional stress relaxation testing device according to claim 1, comprising control means for controlling movement of the gripping means, said control means comprising a gear assembly, a hydraulic drive or a pneumatic drive.

11. A two dimensional stress relaxation testing device according to claim 4, wherein the force detectors are force transducers or strain gauges.

12. A two dimensional stress relaxation testing device according to claim 5, wherein the output means comprise a plurality of output devices selected from the group consisting of a computer interface, a digital display, an analog output and a chart recorder.

13. A method for testing a viscoelastic material comprising (a) providing the apparatus of claim 10;

(b) gripping the viscoelastic material with the first and second pairs of juxtaposed gripping means;

(c) causing the drive means to displace the first and second pairs of gripping means along the respective slideways in said mutually perpendicular directions so as to strain the material;

(d) allowing the material to relax while continuously monitoring forces in the mutually perpendicular directions.

14. A method according to claim 13, wherein the drive means displaces the first and second gripping means at a constant rate.

15. A method according to claim 14, wherein the viscolastic material is selected from the group consisting of leather, a polymer, a textile and rubber.

* * * * *